(12) United States Patent
Choi et al.

(10) Patent No.: US 11,986,248 B2
(45) Date of Patent: May 21, 2024

(54) APPARATUS AND METHOD FOR MATCHING THE REAL SURGICAL IMAGE WITH THE 3D-BASED VIRTUAL SIMULATED SURGICAL IMAGE BASED ON POI DEFINITION AND PHASE RECOGNITION

(71) Applicant: HUTOM CO., LTD., Seoul (KR)

(72) Inventors: Min Kook Choi, Seoul (KR); Seung Bum Hong, Seoul (KR); Nak Jun Sung, Seoul (KR); Ye Jin Han, Seoul (KR); Sung Jae Kim, Seoul (KR)

(73) Assignee: HUTOM CO., LTD., Seoul (KR)

( * ) Notice: Subject to any disclaimer, the term of this patent is extended or adjusted under 35 U.S.C. 154(b) by 265 days.

(21) Appl. No.: 17/389,133

(22) Filed: Jul. 29, 2021

(65) Prior Publication Data

US 2023/0031396 A1 Feb. 2, 2023

(30) Foreign Application Priority Data

Jul. 29, 2021 (KR) ........................ 10-2021-0099678

(51) Int. Cl.
*A61B 34/10* (2016.01)
*G06T 7/73* (2017.01)
*G09B 19/00* (2006.01)

(52) U.S. Cl.
CPC ............... *A61B 34/10* (2016.02); *G06T 7/74* (2017.01); *G09B 19/003* (2013.01);
(Continued)

(58) Field of Classification Search
CPC ................... A61B 34/10; A61B 34/20; A61B 2034/104–105; G06T 7/74;
(Continued)

(56) References Cited

U.S. PATENT DOCUMENTS

2020/0113636 A1 4/2020 Chino et al.
2021/0267691 A1* 9/2021 Lang ..................... A61B 90/37

FOREIGN PATENT DOCUMENTS

KR 10-2019-0099999 A 8/2019
KR 10-2019-0106628 A 9/2019
(Continued)

OTHER PUBLICATIONS

Office Action mailed by the Korean Intellectual Property Office dated Apr. 19, 2023, which corresponds to Korean Patent Application No. 10-2021-0099678 and is related to U.S. Appl. No. 17/389,133.

*Primary Examiner* — Timothy A Musselman
(74) *Attorney, Agent, or Firm* — Studebaker & Brackett PC

(57) ABSTRACT

According to an embodiment of the inventive concept, a method for matching an actual surgical image and a 3D-based virtual surgical simulation environment, which is performed by an apparatus, includes setting POI information during surgery at each of surgery steps in a pre-stored surgical image obtained by performing surgery the same as the actual surgical image, matching the POI information with a virtual pneumoperitoneum model of a patient, which is used for the 3D-based virtual surgical simulation environment, the virtual pneumoperitoneum model being displayed on a UI, recognizing a real-time surgery step of the actual surgical image and determining a location of the POI information for the respective recognized surgery step, and obtaining and displaying image information, which is captured by moving a location of an endoscope inserted into the virtual pneumoperitoneum model to the same location as the determined location of the POI information, through the UI.

13 Claims, 9 Drawing Sheets

(52) U.S. Cl.
CPC ... *A61B 2034/104* (2016.02); *A61B 2034/105* (2016.02); *G06T 2207/20021* (2013.01); *G06T 2207/30101* (2013.01)

(58) Field of Classification Search
CPC .......... G06T 2207/20021; G06T 2207/30101; G09B 19/00; G09B 19/003
See application file for complete search history.

(56) References Cited

FOREIGN PATENT DOCUMENTS

KR         10-2008891 B1   10/2019
KR   10-2020-0011970 A   2/2020

\* cited by examiner

APPARATUS AND METHOD FOR MATCHING THE REAL SURGICAL IMAGE WITH THE 3D-BASED VIRTUAL SIMULATED SURGICAL IMAGE BASED ON POI DEFINITION AND PHASE RECOGNITION

CROSS-REFERENCE TO RELATED APPLICATIONS

A claim for priority under 35 U.S.C. § 119 is made to Korean Patent Application No. 10-2021-0099678 filed on Jul. 29, 2021 in the Korean Intellectual Property Office, the entire contents of which are hereby incorporated by reference.

BACKGROUND

Embodiments of the inventive concept described herein relate to matching an actual surgical image and a 3D-based virtual simulated surgical image, and more particularly, relate to an apparatus and method for matching a 3D-based virtual simulated surgical image and an actual surgical image based on POI definition and phase recognition.

Nowadays, in a case of surgery in a hospital, a 3D virtual simulated surgical environment identical to a patient's surgical condition is generated before surgery instead of immediately proceeding with surgery. Afterward, virtual simulation surgery may be performed under the same condition as actual surgery.

In a case of the virtual simulation surgery, an accurate diagnosis may be prepared in advance. Accordingly, it is possible to make a plan through the virtual simulation surgery without relying on the sense of a specialist, thereby removing even the smallest error.

Portions incapable of being grasped through a human eye may be easily grasped in the virtual simulation surgery. However, unlike the virtual simulation surgery, there may be portions incapable of being grasped through the human eye in actual surgery.

In detail, a specialist who has not performed the corresponding surgery often lacks clinical experience with regard to blood vessels positioned behind organs or portions inside a body that should not be touched during surgery. When the specialist is not fully aware of the information in actual surgery, an emergency situation may occur during surgery.

Accordingly, as if the virtual simulation surgery provides information about the inside of a patient's body that is invisible to the naked eye during actual surgery, it is necessary to provide the information to a specialist performing the surgery in real time.

There is a prior art disclosed as Korean Patent Publication No. 10-2020-0011970.

SUMMARY

Embodiments of the inventive concept provide an apparatus that may recognize a surgery step in a surgical image, may obtain a location of point-of-interest (POI) information for each surgery step from a 3D-based virtual simulated surgical image, and may provide the location of POI information together with the surgical image.

Furthermore, embodiments of the inventive concept provide an apparatus that may provide a 3D-based virtual surgical simulation environment based on a virtual pneumoperitoneum model for predicting a patient's actual pneumoperitoneum status, and may match a 3D-based virtual surgical simulation environment and an actual surgical image. Accordingly, the inventive concept may enable the 3D-based virtual surgical simulation environment to operate as an excellent rehearsal for actual surgery.

The technical problems to be solved by the present inventive concept are not limited to the aforementioned problems, and any other technical problems not mentioned herein will be clearly understood from the following description by those skilled in the art to which the inventive concept pertains.

According to an embodiment, a method for matching an actual surgical image and a 3D-based virtual surgical simulation environment, which is performed by an apparatus, includes setting point-of-interest (POI) information during surgery at each of surgery steps in a pre-stored surgical image obtained by performing surgery the same as the actual surgical image, matching the POI information with a virtual pneumoperitoneum model of a patient, which is used for the 3D-based virtual surgical simulation environment, the virtual pneumoperitoneum model being displayed on a user interface (UI), recognizing a real-time surgery step of the actual surgical image and determining a location of the POI information for the respective recognized surgery step, and obtaining and displaying image information, which is captured by moving a location of an endoscope inserted into the virtual pneumoperitoneum model to the same location as the determined location of the POI information, through the UI.

Herein, the setting of the POI information may include dividing the actual surgical image into one or more basic steps based on a surgery object to divide the actual surgical image into the surgery steps, dividing a surgical operation for a target anatomy or a target object, which corresponds to a surgical purpose of the surgery object, into one or more sub-sections, and dividing one or more unit images included in each of the sub-sections into division sections for each operation by a surgery tool.

Furthermore, the setting of the POI information may include setting the POI information based on the divided sub-sections.

Moreover, the determining of the location of the POI information may include recognizing a basic step corresponding to the real-time surgery step of the actual surgical image based on a deep learning model, recognizing a first sub-section corresponding to the real-time surgery step from among a plurality of sub-sections included in the basic step, determining that one division section corresponding to the real-time surgery step from among a plurality of division sections for the first sub-section corresponds to a time point at which the image information is required, determining the location of the POI information for the respective first sub-section or the location of the POI information for each second sub-section, which is a step immediately following the first sub-section, and matching information about the determined location of the POI information on the virtual pneumoperitoneum model.

Herein, the obtaining of the image information may include moving the location of the endoscope, which is inserted into the virtual pneumoperitoneum model on the UI, based on the determined location of the POI information, obtaining image information corresponding to a corresponding location from the endoscope, and displaying the obtained image information on the UI at the time point.

Also, the matching of the POI information may include obtaining the virtual pneumoperitoneum model of the patient, displaying the virtual pneumoperitoneum model on the UI, inserting the endoscope at a predetermined location of the virtual pneumoperitoneum model, and sequentially matching the POI information with the virtual pneumoperitoneum model in a state where the endoscope is inserted.

Besides, the determining of the location of the POI information may include recognizing the real-time surgery step of the actual surgical image based on a deep learning model, determining the location of the POI information for each recognized surgery step or the location of the POI information for each surgery step immediately following the recognized surgery step, and matching information about the determined location of the POI information on the virtual pneumoperitoneum model. Herein, the obtaining of the image information may include moving the location of the endoscope, which is inserted into the virtual pneumoperitoneum model on the UI, based on the determined location of the POI information, obtaining image information corresponding to a corresponding location from the endoscope, and displaying the obtained image information on the UI in real time.

In addition, the displaying of the obtained image information on the UI may include displaying the image information at a corresponding location of the virtual pneumoperitoneum model and additionally displaying an indicator indicating a description of the image information.

Furthermore, the displaying of the obtained image information on the UI may include rendering and displaying the image information about portions, which are invisible to naked eyes in the actual surgical image, on the UI in real time.

Also, the virtual pneumoperitoneum model may include at least one of an actual organ, a blood vessel, a fat, and a muscle in a pneumoperitoneum status of the patient.

According to an embodiment, an apparatus for matching an actual surgical image and a 3D-based virtual surgical simulation environment includes an acquisition unit that obtains the actual surgical image and a pre-stored surgical image obtained by performing surgery the same as the actual surgical image, a display unit that displays the actual surgical image and a virtual pneumoperitoneum model, a processor that sets POI information during surgery at each surgery step in the pre-stored surgical image, sequentially matches the POI information with a virtual pneumoperitoneum model of a patient, which is used for the 3D-based virtual surgical simulation environment, the virtual pneumoperitoneum model being displayed on a UI, recognizes a real-time surgery step of the actual surgical image and determines a location of the POI information for the respective recognized surgery step, and obtains and displays image information, which is captured by moving a location of an endoscope inserted into the virtual pneumoperitoneum model to the same location as the determined location of the POI information, through the UI.

In addition, another method, another apparatus, and another system for implementing the inventive concept, and a computer-readable recording medium for recording a computer program for performing the method may be further provided.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
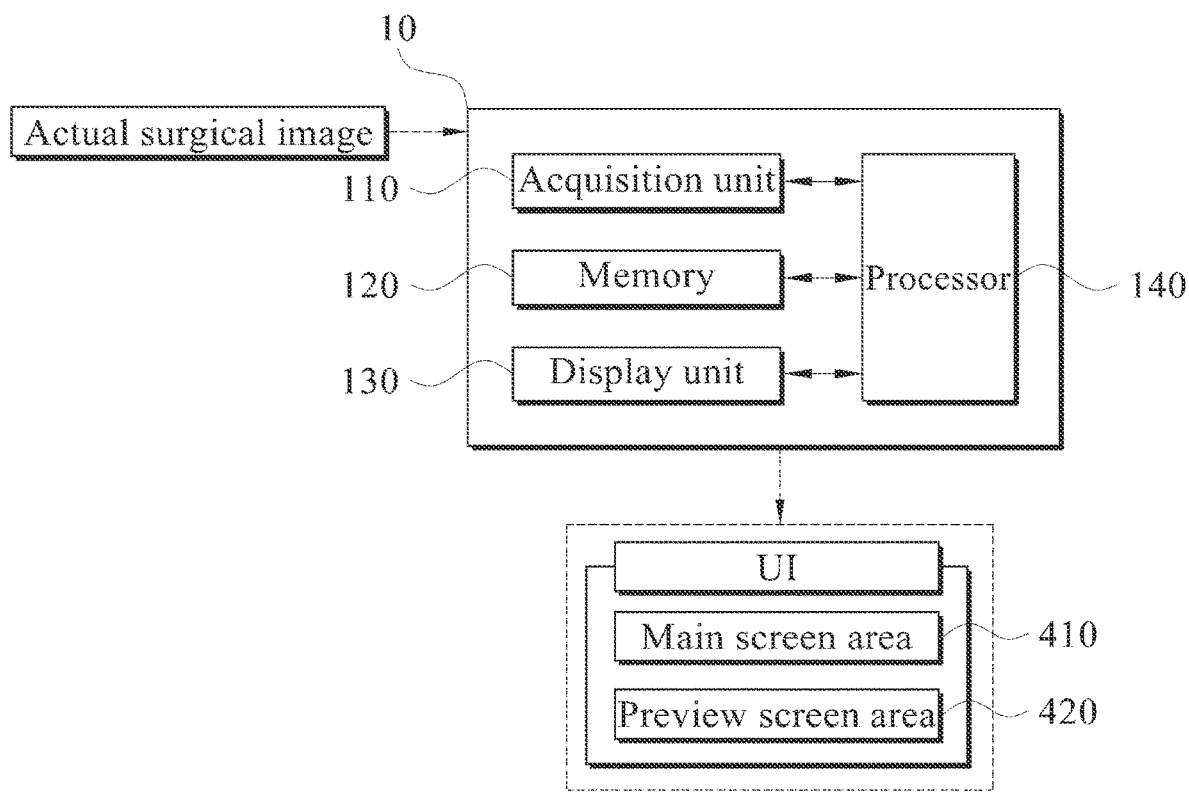
FIG. 1 is a diagram schematically illustrating an apparatus 10 for matching an actual surgical image and a 3D-based virtual surgical simulation environment, according to an embodiment of the inventive concept.

The above and other aspects, features and advantages of the inventive concept will become apparent from the following description of the following embodiments given in conjunction with the accompanying drawings. The inventive concept, however, may be embodied in various different forms, and should not be construed as being limited only to the illustrated embodiments. Rather, these embodiments are provided as examples so that the inventive concept will be thorough and complete, and will fully convey the concept of the inventive concept to those skilled in the art. The inventive concept may be defined by scope of the claims.

The terminology used herein is for the purpose of describing embodiments and is not intended to limit the inventive concept. In the specification, the singular forms include plural forms unless particularly mentioned. The terms "comprises" and/or "comprising" used herein does not exclude presence or addition of one or more other elements, in addition to the aforementioned elements. The same reference numerals denote the same elements throughout the specification. As used herein, the term "and/or" includes any and all combinations of one or more of the associated components. It will be understood that, although the terms "first", "second", etc., may be used herein to describe various components, these components should not be limited by these terms. These terms are only used to distinguish one component from another component. Thus, a first component discussed below could be termed a second component without departing from the teachings of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

Hereinafter, embodiments of the inventive concept will be described in detail with reference to accompanying drawings.

FIG. 1 is a diagram schematically illustrating an apparatus 10 for matching an actual surgical image and a 3D-based virtual surgical simulation environment, according to an embodiment of the inventive concept.

Figure 2:
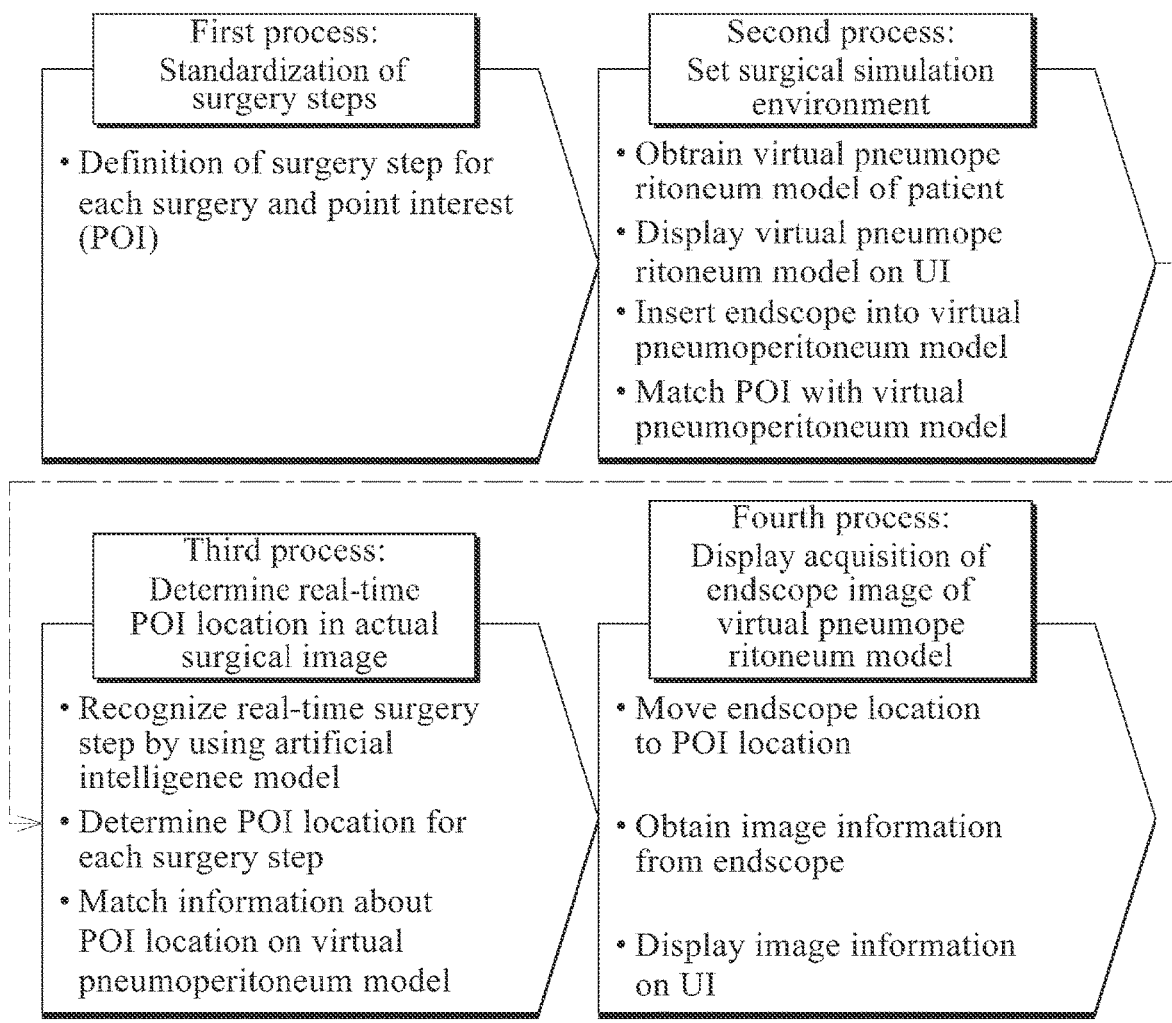
FIG. 2 is a view for describing a process for matching an actual surgical image and a 3D-based virtual surgical simulation environment, according to an embodiment of the inventive concept.

FIG. 2 is a view for describing a process for matching an actual surgical image and a 3D-based virtual surgical simulation environment, according to an embodiment of the inventive concept.

Figure 3:
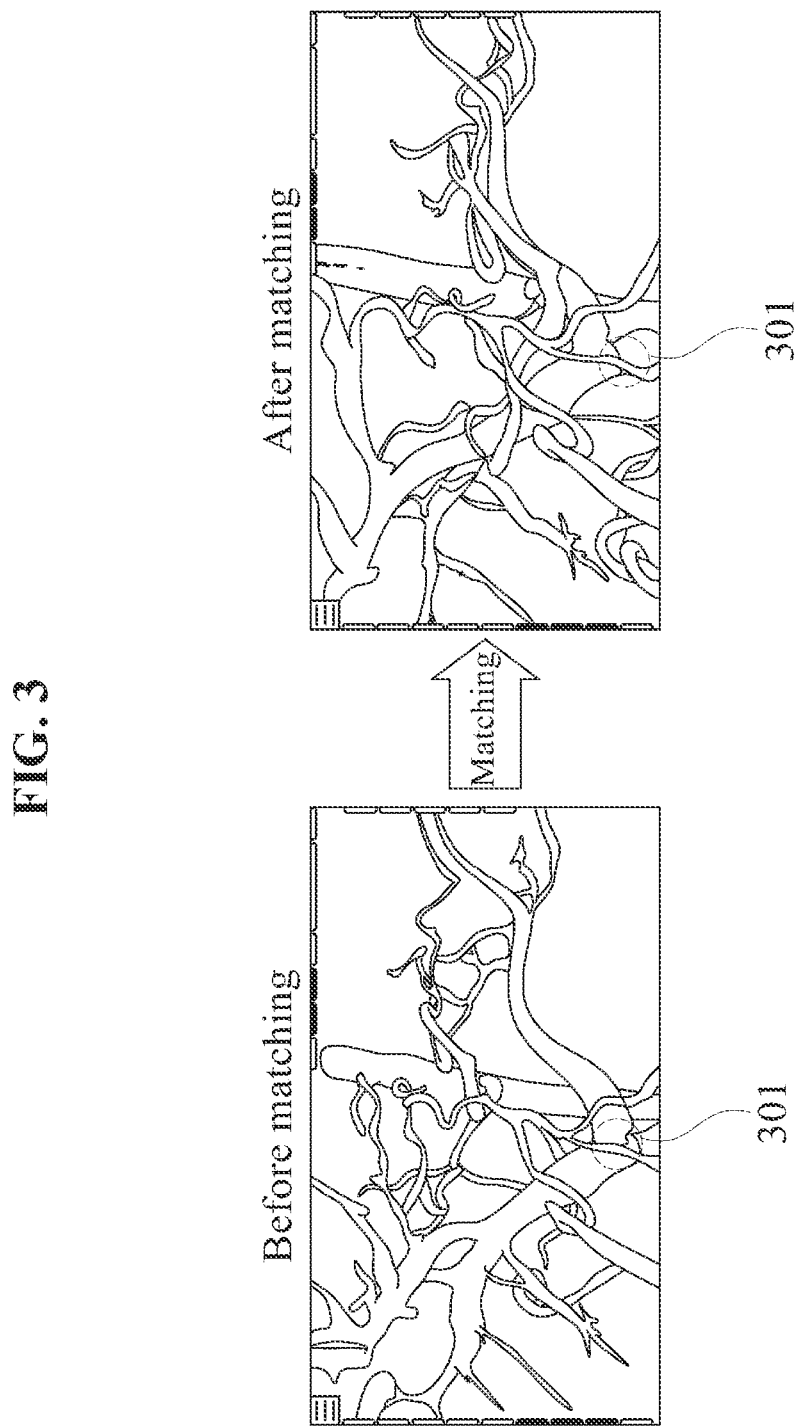
FIG. 3 is an exemplary view illustrating vascular matching in a virtual pneumoperitoneum model, according to an embodiment of the inventive concept.

FIG. 3 is an exemplary view illustrating vascular matching in a virtual pneumoperitoneum model, according to an embodiment of the inventive concept.

Figure 4:
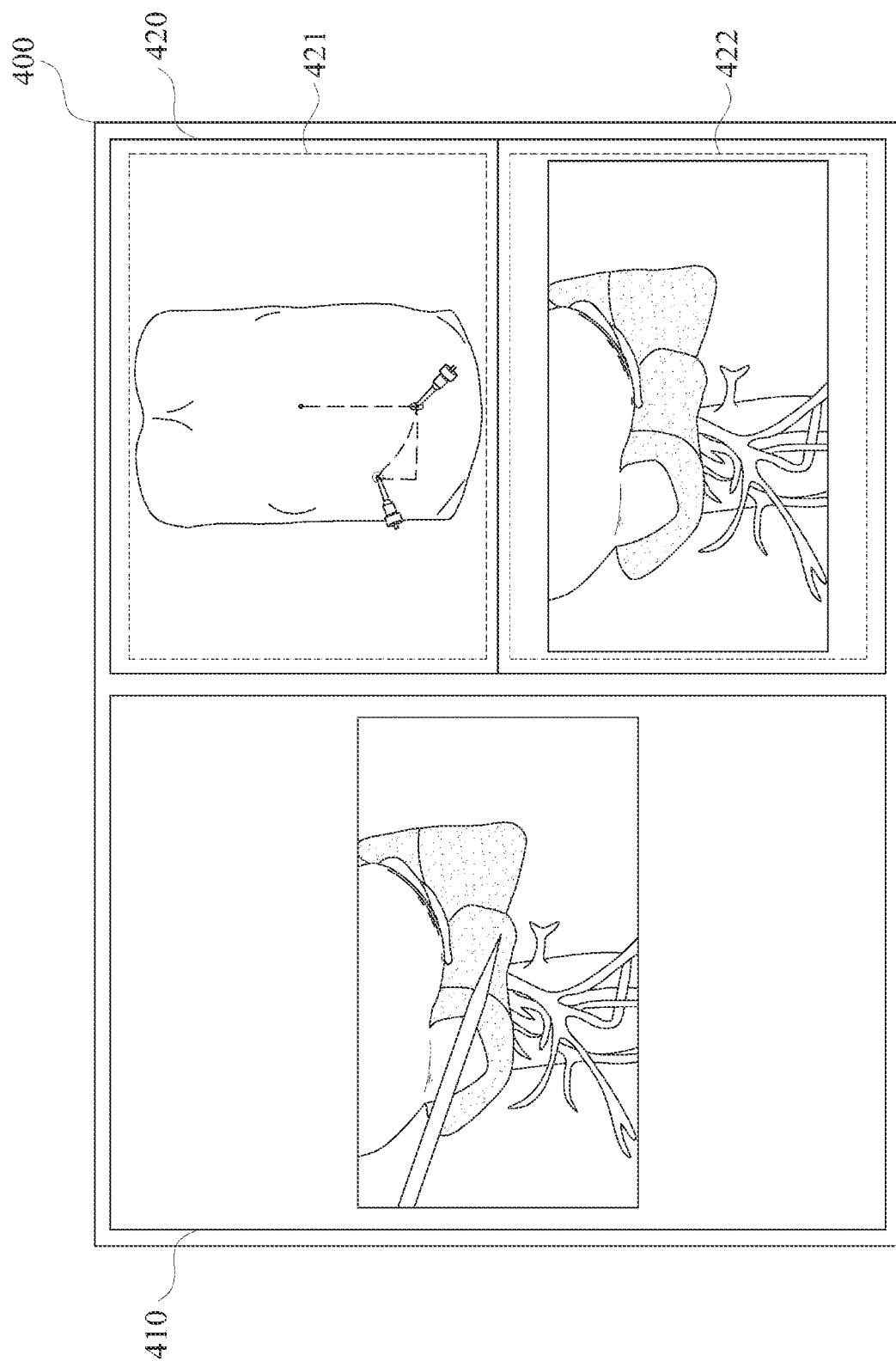
FIG. 4 is an exemplary view of a UI illustrating a 3D-based virtual surgical simulation environment, according to an embodiment of the inventive concept.

FIG. 4 is an exemplary view of a UI illustrating a 3D-based virtual surgical simulation environment, according to an embodiment of the inventive concept.

Figure 5:
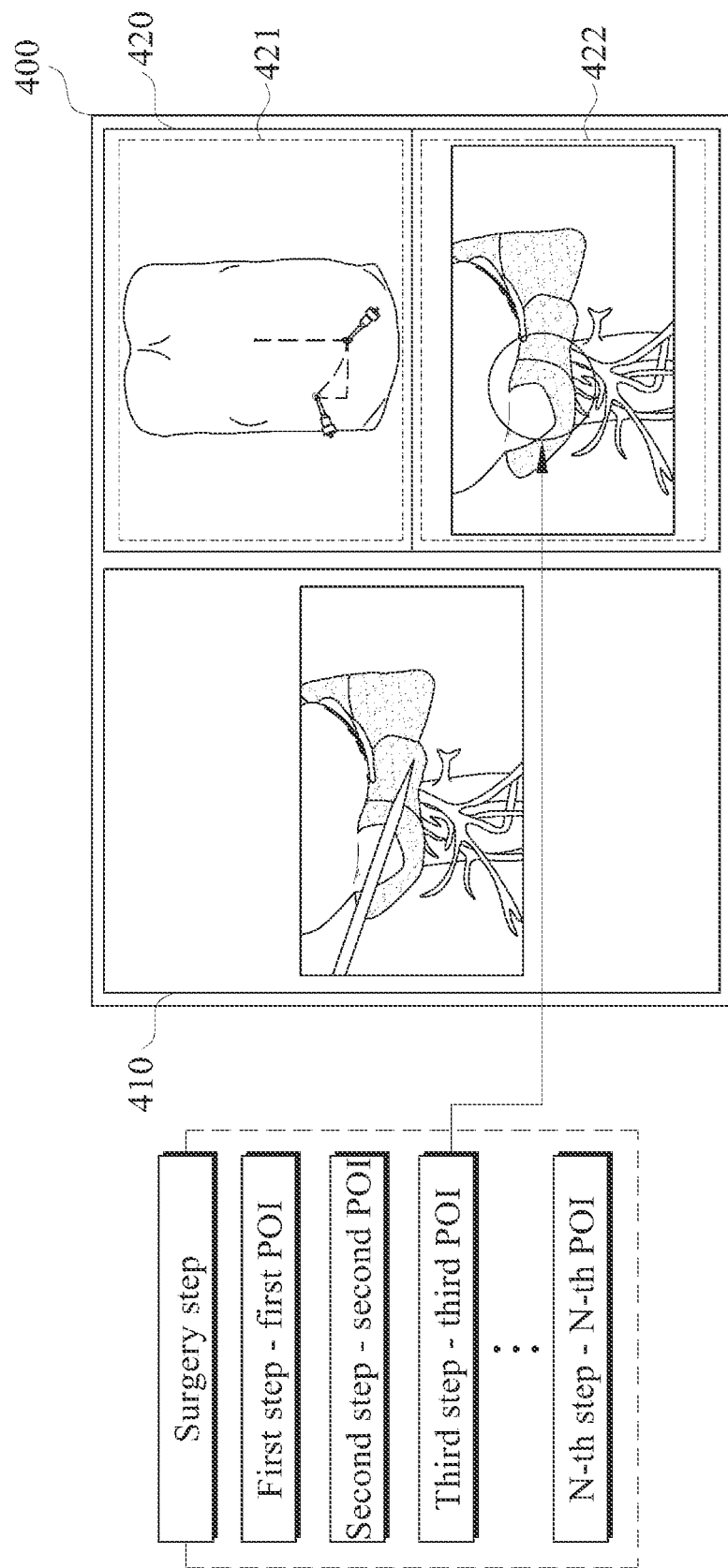
FIG. 5 is a view for describing moving a location of an endoscope inserted into a virtual pneumoperitoneum model to a location of POI information at a surgery step in an actual surgical image, according to an embodiment of the inventive concept.

FIG. 5 is a view for describing moving a location of an endoscope inserted into a virtual pneumoperitoneum model to a location of POI information at a surgery step in an actual surgical image, according to an embodiment of the inventive concept.

Figure 6:
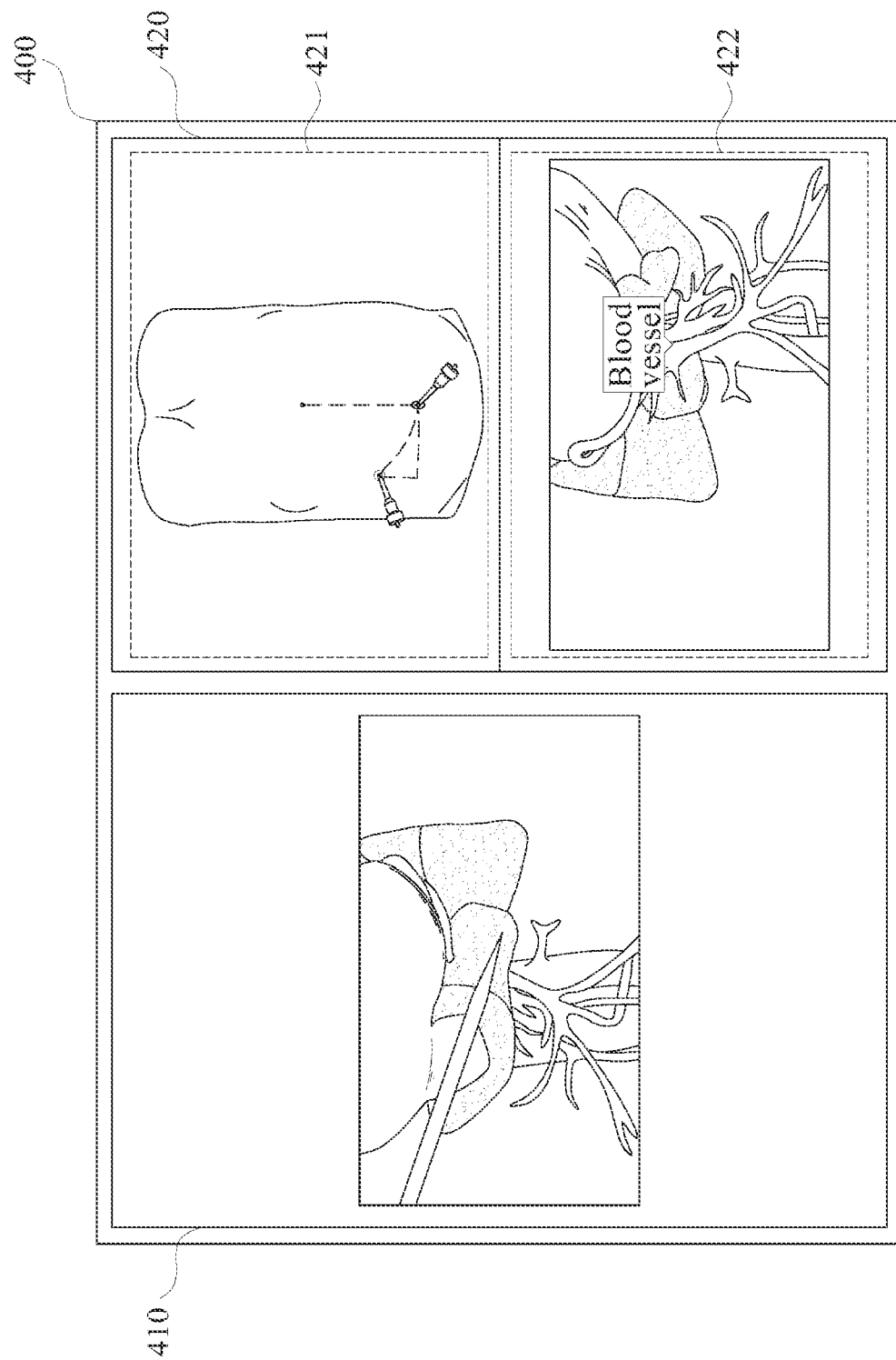
FIG. 6 is an exemplary view for describing that an image captured through an endoscope inserted into a virtual pneumoperitoneum model is displayed on a UI together with an actual surgical image in real time, according to an embodiment of the inventive concept.

FIG. 6 is an exemplary view for describing that an image captured through an endoscope inserted into a virtual pneumoperitoneum model is displayed on a UI together with an actual surgical image in real time, according to an embodiment of the inventive concept.

Figure 7:
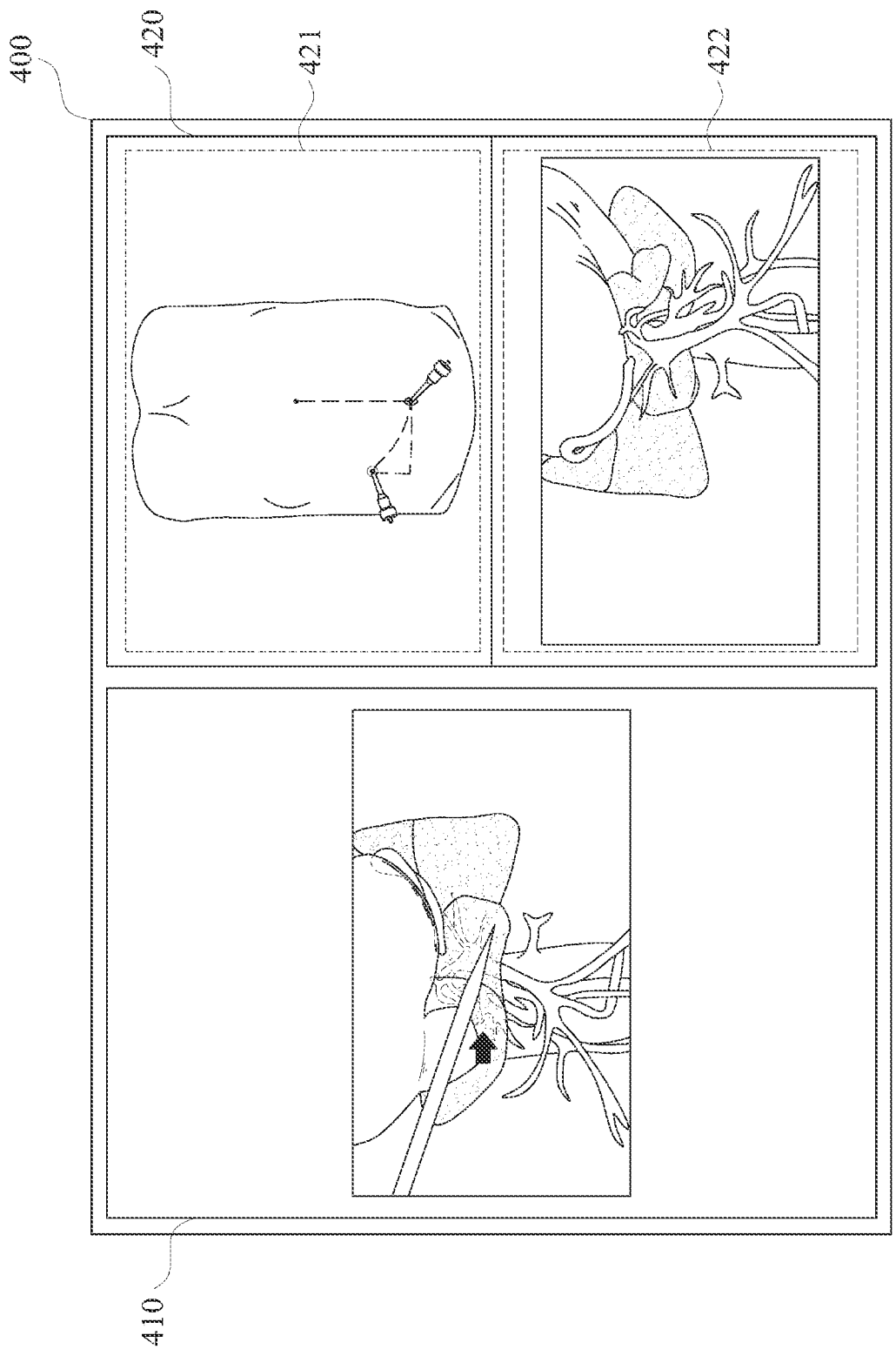
FIG. 7 is an exemplary view for describing that an image captured through an endoscope inserted into a virtual pneumoperitoneum model is displayed on a UI so as to be overlaid on an actual surgical image, according to an embodiment of the inventive concept.

FIG. 7 is an exemplary view for describing that an image captured through an endoscope inserted into a virtual pneumoperitoneum model is displayed on a UI so as to be overlaid on an actual surgical image, according to an embodiment of the inventive concept.

Hereinafter, according to an embodiment of the inventive concept, the apparatus 10 for matching an actual surgical image and a virtual simulated surgical image will be described with reference to FIGS. 1 to 7.

Medical staff may desire to secure countermeasures against various variables capable of occurring during actual surgery by performing virtual simulation on surgery in advance before actual surgery. As the countermeasure against the various variables, 3D-based virtual surgery simulation may be provided within the same virtual surgery environment as an actual surgery environment.

Portions incapable of being grasped through a human eye may be easily grasped through the virtual 3D-based virtual surgery simulation.

However, during actual surgery, there are portions incapable of being grasped through the human eye as it is.

In detail, a specialist who has not performed the corresponding surgery often lacks clinical experience with regard to blood vessels positioned behind organs or portions that should not be touched during surgery. When the specialist is not fully aware of the information in actual surgery, an emergency situation may occur during surgery.

Accordingly, as if the virtual simulation surgery provides information about the inside of a patient's body that is invisible to the naked eye during actual surgery, the apparatus 10 may provide the information to a specialist performing the surgery in real time.

The apparatus 10 may recognize a surgery step in a surgical image, may obtain a location of POI information for each surgery step from a 3D-based virtual simulated surgical image, and may provide the location of POI information together with the surgical image. Accordingly, even a specialist who lacks experience in the corresponding surgery may receive an excellent surgical guide in real time, thereby improving a success rate of surgery and significantly reducing the risk of surgery.

Furthermore, the apparatus 10 may provide an excellent guide to an expert performing surgery by providing a 3D-based virtual surgical simulation environment based on a virtual pneumoperitoneum model, in which a patient's actual pneumoperitoneum status is predicted, and matching a 3D-based virtual surgical simulation environment and an actual surgical image.

Herein, the apparatus 10 may include all various devices capable of providing results to a user by performing arithmetic processing.

That is, the apparatus 10 may be in a form of a computer. In detail, the computer may include all various devices capable of providing results to a user by performing arithmetic processing.

For example, the computer may correspond to not only a desktop personal computer (PC) or a notebook but also a smart phone, a tablet PC, a cellular phone, a personal communication service (PCS) phone, a mobile terminal of a synchronous/asynchronous International Mobile Telecommunication-2000 (IMT-2000), a palm PC, a personal digital assistant (PDA), and the like. Besides, when a head mounted display (HMD) device includes a computing function, the HMD device may be a computer.

Furthermore, the computer may correspond to a server that receives a request from a client and processes information.

Moreover, referring to FIGS. 1 and 2, the apparatus 10 may include an acquisition unit 110, a memory 120, a display unit 130, and a processor 140. Herein, the apparatus 10 may include fewer or more components than the components illustrated in FIG. 1.

The acquisition unit 110 may include one or more modules that enable wireless communication between the apparatus 10 and an external device (not shown), between the apparatus 10 and an external server (not shown), or between the apparatus 10 and a communication network (not shown).

Herein, the acquisition unit 110 may include one or more modules connecting the apparatus 10 to one or more networks.

The acquisition unit 110 may obtain a virtual pneumoperitoneum model used for 3D-based virtual surgery simulation from the external server (not shown) or the memory 120.

Herein, the external device (not shown) may be a medical image capturing device that captures medical image data (hereinafter, 3D image data of abdomen). Herein, the medical image data may include all medical images capable of realizing a patient's body as a 3D model.

Besides, the medical image data may include at least one of a computed tomography (CT) image, a magnetic resonance imaging (MRI) image, and a positron emission tomography (PET) image.

In addition, the external server (not shown) may be a server that stores a virtual pneumoperitoneum model for each patient, medical data for each patient, surgical image for each patient, and the like for a plurality of patients.

Herein, the medical data for each patient may include data associated with at least one of a patient's age, a patient's gender, a patient's height, a patient's weight, a patient's body mass index, and whether a patient has experience of childbirth.

Furthermore, a communication network (not shown) may transmit or receive various pieces of information between the apparatus 10, the external device (not shown), and the external server (not shown). Various types of communication networks may be used. For example, wireless communication methods such as wireless LAN (WLAN), Wi-Fi, Wibro, Wimax, High Speed Downlink Packet Access (HSDPA), and the like or wired communication methods such as Ethernet, xDSL (ADSL or VDSL), Hybrid Fiber Coax (HFC), Fiber to The Curb (FTTC), Fiber To The Home (FTTH), and the like may be used in a communication network.

In the meantime, the communication network is not limited to the communication method described above, and may include all types of communication methods widely known or to be developed in the future in addition to the above communication methods.

The memory 120 may store data for supporting various functions of the apparatus 10. The memory 120 may store a plurality of application programs (or applications) running in the apparatus 10, data for an operation of the apparatus 10, and instructions. At least part of the application programs may be present for basic functions of the apparatus 10. In the meantime, the application program may be stored in the memory 120, may be installed in the apparatus 10, and may be driven by the processor 140 so as to perform an operation (or function) of the apparatus 10.

In addition, the memory 120 may include a plurality of processes for matching an actual surgical image and a 3D-based virtual surgical simulation environment, according to an embodiment of the inventive concept. Herein, the plurality of processes will be described below when an operation of the processor 140 is described.

The memory 120 may store a virtual pneumoperitoneum model for each of a plurality of patients and a surgical image for each of a plurality of patients. Herein, the virtual pneumoperitoneum model may be generated through the processor 140 and stored in the memory 120. Alternatively, the virtual pneumoperitoneum model may be obtained from the external server (not shown) and stored in the memory 120.

In addition, the virtual pneumoperitoneum model may include at least one of an actual organ, blood vessel, fat, and muscle in the patient's pneumoperitoneum status.

The display unit 130 may have a mutual layer structure with the touch sensor or may be integrally formed with the touch sensor. Accordingly, a touch screen may be implemented. The touch screen may provide an input interface between the apparatus 10 and a user.

The display unit 130 may display the actual surgical image and the virtual pneumoperitoneum model.

In addition to an operation associated with the application program, the processor 140 may generally control overall operations of the apparatus 10. The processor 140 may provide or process appropriate information or functions to a user, by processing a signal, data, information, or the like, which is input or output through the above-described components, or driving the application program stored in the memory 120.

Besides, the processor 140 may control at least part of the components described with reference to FIG. 1 to operate the application program stored in the memory 120. Furthermore, the processor 140 may combine and operate at least two or more of the components included in the apparatus 10 to operate the application program.

The processor 140 may set POI information during surgery at each surgery step in a pre-stored surgical image obtained by performing the same surgery as the actual surgical image depending on an expert's input.

Herein, the POI information may include information about at least one of blood vessels, organs, and skin to be importantly identified during surgery, and may be set depending on an input of an expert.

In detail, the POI information includes the type (e.g., an arrow, an asterisk, a circle, or the like) of an indicator indicating POI in at least one of a real-time surgical image and a virtual pneumoperitoneum model, a displayed location (coordinates) of POI information in at least one of the real-time surgical image and the virtual pneumoperitoneum model, and detailed information (precautions during surgery, cautions associated with surgery, notifications, and the like at the corresponding surgery step set by an expert are displayed as text images) about POI information.

In detail, the POI information about blood vessels may include at least one of bifurcation of blood vessels, bifurcation of arteries, or bifurcation of veins.

That is, the expert may define surgery steps based on pre-stored surgical images depending on the type of surgery, and may assign POI information, which is a point of interest for each surgery step.

Herein, the processor 140 may receive and set POI information from the expert during surgery at each surgery step in the pre-stored surgical image based on the first process among a plurality of processes.

In more detail, to divide the surgical image into surgery steps depending on an input of the expert, the processor 140 may divide the surgery steps into one or more basic steps based on a surgery object. Herein, the surgery object may be an organ or lesion on which surgery is performed.

In detail, the processor 140 may divide the surgical image in units of organs depending on the purpose of the surgical operation for a surgery object based on the expert's input and may divide the surgical image into surgery types depending on the purpose of the surgical operation for the surgery object.

Also, the processor 140 may divide directionality included in the surgical image depending on the purpose of the surgical operation for the surgery object based on the expert's input.

Moreover, the processor 140 may divide a plurality of unit images included in the basic step into main sections depending on the expert's input.

Herein, locations of the surgery tools may be determined depending on a specific criterion, definition, or goal of how to perform surgery on the surgery object based on the expert's input. Accordingly, the processor 140 may divide the plurality of unit images included in the basic step into the main sections.

Also, the processor 140 may divide the main section depending on a surgical operation corresponding to a surgery purpose for the surgery object into one or more sub-sections based on the expert's input.

Herein, the processor 140 may set the POI information based on the divided sub-section depending on the expert's input.

More specifically, the processor 140 may divide a main section into sub-sections having one or more layers based on a target anatomy or target object on which an operation is performed by the surgery tool.

That is, the processor 140 may divide the main section into a tissue transformation or a basic action depending on the purpose of the surgery performed on a specific target anatomy or a specific target object.

Moreover, the processor 140 may determine the unit image included in each sub-section as the specific unit operation and may divide the unit image into key movements.

Herein, the target anatomy is an anatomical portion treated during surgery. The target object may include at least one of materials, which are used in an operating room and which are necessary for surgery, for example, a metal clip, a platelet clip, a suture, a needle, gauze, and a drain hole.

Afterward, the processor 140 may divide one or more unit images included in each sub-section into division sections for each operation by a surgery tool depending on the expert's input.

In more detail, the processor 140 may determine that the one or more unit images included in each sub-section is a specific unit operation, depending on the expert's input and may divide the one or more unit images into key movements. In addition, the processor 140 may determine that a single operation of a single surgical tool as a unit operation and may divide the one or more unit images into the division sections.

In detail, in accordance with the purpose of the surgery, the processor 140 may divide one or more unit images into first single operations depending on the spatial coordinate movement of the surgical tool in the surgical image based on the expert's input.

Moreover, in accordance with the purpose of the surgery, the processor 140 may divide one or more unit images into second single operations depending on the movement of a joint of the surgical tool in spatial coordinates based on the expert's input.

Besides, in accordance with the purpose of the surgery, the processor 140 may divide one or more unit images into third single operations depending on the movement of the surgical tool in the surgical image based on the expert's input.

Herein, the processor 140 may set POI information during surgery at each surgery step based on the divided division sections depending on the expert's input.

As such, the processor 140 may subdivide the surgery step of the surgical image depending on the expert's input and may set POI information during surgery for each sub-section among the subdivided surgery steps.

The processor 140 may match the POI information with the patient's virtual pneumoperitoneum model used in a 3D-based virtual surgical simulation environment. The virtual pneumoperitoneum model may be displayed on a user interface (UI).

Herein, the processor 140 may match the POI information with the patient's virtual pneumoperitoneum model based on the second process among the plurality of processes.

In detail, first of all, the processor 140 may obtain or generate the patient's virtual pneumoperitoneum model through the memory 120 or an external server (not shown).

The virtual pneumoperitoneum model may be generated by the processor 140 to predict the patient's actual pneumoperitoneum status based on the patient's status data, pieces of landmark data, and the patient's body data.

Herein, the status data may include data associated with at least one of a patient's age, a patient's gender, a patient's height, a patient's weight, a patient's body mass index, and whether a patient has experience of childbirth.

In addition, the pieces of landmark data may be displayed on 3D image data of the patient's abdomen.

Furthermore, the pieces of cross-sectional image data are cross-sections at locations where the pieces of landmark data are displayed. The body data may include at least one of a ratio of height and width to the patient's body in the pieces of cross-sectional image data, the patient's skin circumference, a direction and distance to anterior-posterior of the patient's body, the patient's fat region, and the patient's muscle region.

Herein, when generating the virtual pneumoperitoneum model, the processor 140 may realize a blood vessel having a state the same as the state of the blood vessel in the patient's actual pneumoperitoneum status.

In detail, when generating the virtual pneumoperitoneum model, the processor 140 may use EAP image to divide/restore an artery on a CT image, and may use a PP image to divide/restore a vein on the CT image.

Herein, when the EAP and PP images are captured, the patient's location may be different, and thus matching may be required.

Accordingly, the processor 140 may additionally divide/restore main portions of the artery when the vein is divided/restored. The processor 140 may adjust the location of the artery so as to match major portions of the artery on the vein.

Herein, referring to FIG. 3, the processor 140 may match the vein and the artery depending on a major portion 301 of the artery based on the expert's manipulation. Alternatively, the processor 140 may automatically match the vein and the artery.

Herein, the major portion 301 of the artery may be POI information, and may be a bifurcation of the artery.

As such, even the appearance of blood vessels in the virtual pneumoperitoneum model may be realized to be the same as the appearance of blood vessels in the patient's actual pneumoperitoneum status. Accordingly, the processor 140 may prevent accidents during surgery by providing the expert with image information obtained from an endoscope inserted into the virtual pneumoperitoneum model with respect to POI information (e.g., the bifurcation of a blood vessel) for each surgery step.

In addition, the processor 140 may display the virtual pneumoperitoneum model on a user interface (UI).

Herein, referring to FIG. 4, a UI 400 may include a main screen area 410 and a preview screen area 420.

In detail, the main screen area 410 may be an area in which an actual surgical image captured in real time through an endoscope inserted into the patient's body during actual surgery are displayed.

Furthermore, the preview screen area 420 may include a first area 421 where the virtual pneumoperitoneum model is displayed through a plan view and a second area 422 where an internal image of the virtual pneumoperitoneum model captured through the endoscope inserted through a reference trocar of the virtual pneumoperitoneum model is displayed.

That is, the processor 140 may simultaneously output the first area 421, which is displayed when the surface of the pneumoperitoneum model is viewed from the top, and the second area 422, which is captured through the inserted camera (endoscope), on the UI 400.

Herein, the first area 421 may be a screen displayed when the surface of the pneumoperitoneum model is viewed from the top. Also, information of a tool inserted through at least one trocar of the virtual pneumoperitoneum model may be displayed in the first area 421.

The second area 422 may be an area in which an internal image of the virtual pneumoperitoneum model captured through the endoscope inserted through the reference trocar is displayed.

Moreover, a screen, which is displayed when a tool inserted into the at least one trocar enters the inside of the virtual pneumoperitoneum model, may be captured through the endoscope and may be displayed in the second area 422 in real time.

Next, the processor 140 may insert the endoscope at a preset location of the virtual pneumoperitoneum model.

In detail, the processor 140 may insert the endoscope at a lower portion of a navel of the virtual pneumoperitoneum model through a trocar inserted at a location separated by a preset interval.

Next, the processor 140 may sequentially match the POI information with the virtual pneumoperitoneum model in a state where the endoscope is inserted.

In detail, the processor 140 may sequentially match the POI information for each surgery step with the virtual pneumoperitoneum model in a state, in which the endoscope is inserted, based on image information obtained through the endoscope. The processor 140 may recognize a real-time surgery step of the actual surgical image and may determine a location of POI information for each surgery step thus recognized.

Herein, the processor 140 may recognize the real-time surgery step of the actual surgical image based on the third process among a plurality of processes and may determine the location of POI information for each surgery step thus recognized.

Referring to FIG. 5, first of all, the processor 140 may recognize the real-time surgery step of the actual surgical image based on a deep learning model.

Herein, the deep learning model may include, but is not limited to, a convolutional neural network (CNN) (hereinafter referred to as "CNN"), and may be formed of neural networks of various structures.

For example, the processor 140 may recognize that a current time point among the real-time surgery steps (first to N-th steps) of the actual surgical image is the third step, based on the deep learning model.

Next, when the real-time surgery step corresponding to the current time point is recognized, the processor 140 may search for POI information corresponding to the recognized real-time surgery step or POI information corresponding to the next surgery step of the recognized real-time surgery step from among pieces of POI information for each surgery step set for the pre-stored surgical image, may extract the found POI information, and may display a portion corresponding to the extracted POI information in the virtual pneumoperitoneum model. Herein, a plurality of surgery steps may be included in the pre-stored surgical image obtained by performing the same surgery as the actual surgical image. The POI information may be set for each (or some) of the plurality of surgery steps.

The processor 140 may distinguish each real-time surgery step from the actual surgical image.

That is, the processor 140 may recognize a current surgery step or a surgery step, which is ahead of one step, from the actual surgical image.

Afterward, the processor 140 may determine whether POI information is set for the surgery step corresponding to the recognized surgery step in the pre-stored surgical image.

Next, the processor 140 may match information about the determined location of the POI information on the virtual pneumoperitoneum model.

Herein, the processor 140 may match the information about the determined location of the POI information with a location of the POI information, which is indicated by a circular indicator displayed on the second area 422 where a screen is displayed through the camera (endoscope).

Alternatively, the processor 140 may recognize a basic step corresponding to a real-time surgery step of the actual surgical image based on the deep learning model.

Moreover, the processor 140 may recognize a first sub-section corresponding to the real-time surgery step among a plurality of sub-sections included in the basic step.

Afterward, the processor 140 may determine that one division section corresponding to the real-time surgery step from among the plurality of division sections for the first sub-section corresponds to a time point at which the image information is required.

Also, the processor 140 may determine the location of the POI information for each first sub-section or the location of the POI information for each second sub-section, which is a step immediately following the first sub-section.

Afterward, the processor 140 may match information about the determined location of the POI information on the virtual pneumoperitoneum model.

The processor 140 may obtain and display image information, which is captured by moving a location of an endoscope inserted into the virtual pneumoperitoneum model to the same location as the determined location of the POI information, through the UI 400.

Herein, the processor 140 may obtain and display image information, which is captured from the endoscope moved to the same location as the determined location of the POI information, on the UI 400 based on the fourth process among the plurality of processes.

In more detail, first of all, the processor 140 may move the location of the endoscope, which is inserted into the virtual pneumoperitoneum model, on the UI 400 based on the determined location of the POI information.

Next, the processor 140 may obtain image information about the corresponding location from the endoscope.

Next, the processor 140 may display the obtained image information on the UI 400 in real time.

Accordingly, the processor 140 may obtain images of portions, which are invisible in an actual surgical image, through the endoscope inserted into the virtual pneumoperitoneum model.

Herein, referring to FIG. 6, the processor 140 may display the image information obtained from the endoscope at a corresponding location of the virtual pneumoperitoneum model on the UI 400. In addition, the processor 140 may further display an indicator indicating a "blood vessel" that is a description of the image information.

Alternatively, referring to FIG. 7, the processor 140 may render and display the image information about portions, which are invisible to naked eyes in the actual surgical image, on the UI 400 in real time.

Herein, the processor 140 may render (a location and shape of a blood vessel are indicated by a dotted line, and the corresponding portion is indicated by an arrow) and display a blood vessel, which is located behind an organ, on the main screen area 410 of FIG. 6 based on image information obtained from the endoscope inserted into the virtual pneumoperitoneum model.

Figure 8:
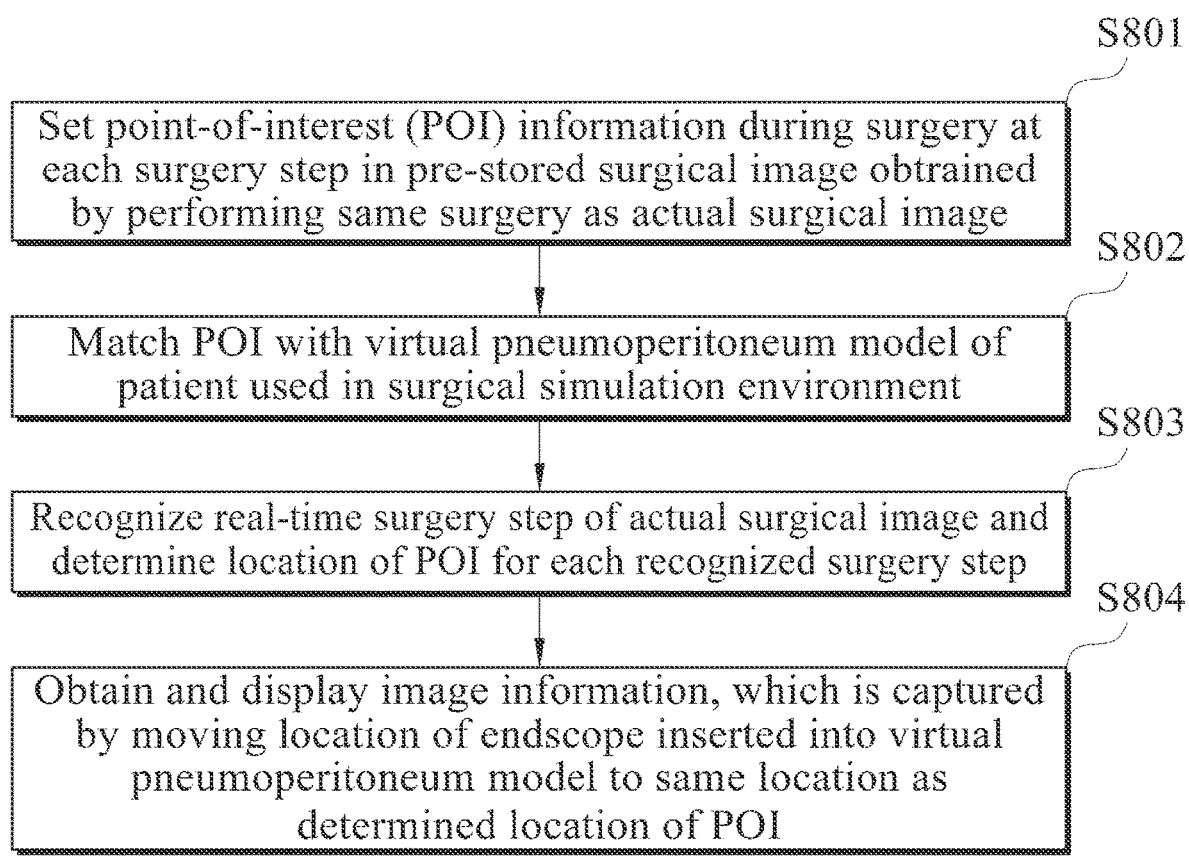
FIG. 8 is a flowchart illustrating a process of matching an actual surgical image and a 3D-based virtual surgical simulation environment, according to an embodiment of the inventive concept.

FIG. 8 is a flowchart illustrating a process of matching an actual surgical image and a 3D-based virtual surgical simulation environment, according to an embodiment of the inventive concept. Herein, an operation of the processor 140 may be performed by the apparatus 10.

The processor 140 may set POI information during surgery at each surgery step in a pre-stored surgical image obtained by performing the same surgery as the actual surgical image depending on an expert's input (S801).

In detail, to divide the surgical image into surgery steps depending on an input of the expert, the processor 140 may divide the surgery steps into one or more basic steps based on a surgery object.

Moreover, the processor 140 may divide a plurality of unit images included in the basic step into main sections depending on the expert's input.

Herein, locations of the surgery tools may be determined depending on a specific criterion, definition, or goal of how to perform surgery on the surgery object based on the expert's input. Accordingly, the processor 140 may divide the plurality of unit images included in the basic step into the main sections.

Also, the processor 140 may divide the main section depending on a surgical operation corresponding to a surgery purpose for the surgery object into one or more sub-sections based on the expert's input.

Moreover, the processor 140 may divide one or more unit images included in each sub-section into division sections for each operation by a surgery tool depending on the expert's input.

Herein, the processor 140 may set the POI information based on the divided sub-section depending on the expert's input.

The processor 140 may match the POI information with a patient's virtual pneumoperitoneum model used in a 3D-based virtual surgical simulation environment (S802).

In detail, the processor 140 may obtain the virtual pneumoperitoneum model for the patient from the memory 120 or an external server (not shown), and may display the virtual pneumoperitoneum model on the UI.

Herein, the virtual pneumoperitoneum model may be displayed on the UI, and may include at least one of an actual organ, blood vessel, fat, and muscle in the patient's pneumoperitoneum status.

Moreover, the processor 140 may insert the endoscope at a predetermined location of the virtual pneumoperitoneum model, and may sequentially match the POI information with the virtual pneumoperitoneum model in a state where the endoscope is inserted.

The processor 140 may recognize a real-time surgery step of the actual surgical image and may determine a location of POI information for each surgery step thus recognized (S803).

In in detail, the processor 140 may recognize the real-time surgery step of the actual surgical image based on a deep learning model and then may determine a location of the POI information for each recognized surgery step or a location of the POI information for each surgery step immediately following the recognized surgery step.

Afterward, the processor 140 may match information about the determined location of the POI information on the virtual pneumoperitoneum model.

The processor 140 may obtain and display image information, which is captured by moving a location of an endoscope inserted into the virtual pneumoperitoneum model to the same location as the determined location of the POI information, through a UI (S804).

In detail, the processor 140 may move the location of the endoscope, which is inserted into the virtual pneumoperitoneum model, on a UI based on the determined location of the POI information, and may obtain image information about the corresponding location from the endoscope.

Moreover, the processor 140 may display the obtained image information on the UI in real time.

At this time, the processor 140 may display the image information at a corresponding location of the virtual pneumoperitoneum model. In addition, the processor 140 may further display an indicator indicating the description of the image information.

Alternatively, the processor 140 may render and display the image information about portions, which are invisible to naked eyes in the actual surgical image, on the UI in real time.

FIG. 8 illustrates that operation S801 to operation S804 are performed sequentially. However, this is merely illustrative of the technical idea of the inventive concept. Those skilled in the art to which an embodiment of the inventive concept belongs may apply various modifications and variations by changing and performing the order illustrated in FIG. 8 or performing one or more of operation S801 to operation S804 in parallel without departing from the essential characteristics of an embodiment of the inventive concept. The embodiment in FIG. 8 is not limited to a time-series order.

Figure 9:
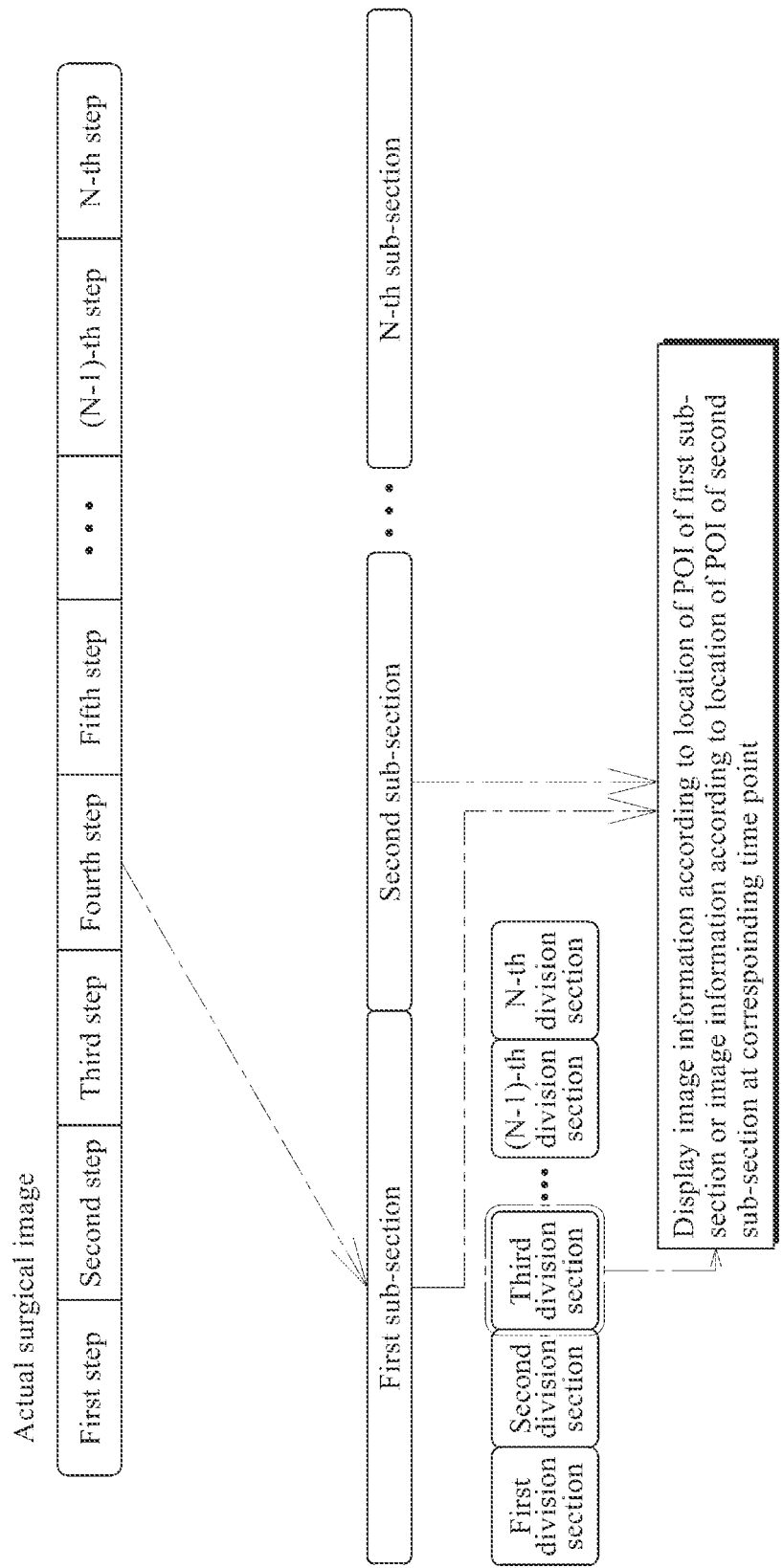
FIG. 9 is an exemplary diagram for describing a process in which a processor determines a location of POI information, according to an embodiment of the inventive concept.

FIG. 9 is an exemplary diagram for describing a process in which the processor 140 determines a location of POI information, according to an embodiment of the inventive concept.

First of all, the processor 140 may recognize a basic step corresponding to a real-time surgery step of the actual surgical image.

Moreover, the processor 140 may recognize a first sub-section corresponding to a fourth step that is the real-time surgery step among a plurality of sub-sections included in the basic step.

Afterward, the processor 140 may determine that a third division section corresponding to the real-time surgery step from among the plurality of division sections for the first sub-section corresponds to a time point at which the image information obtained through the virtual pneumoperitoneum model is required.

Herein, the time point may be just before a point, at which the POI information is located, appears during surgery.

Also, the processor 140 may determine the location of the POI information for each first sub-section or the location of the POI information for each second sub-section, which is a step immediately following the first sub-section. Herein, the POI information may be the bifurcation of a vein.

Afterward, the processor 140 may display image information obtained from the endoscope inserted into the virtual pneumoperitoneum model based on the determined location of the POI information for each first sub-section on a UI.

That is, the processor 140 may display the image information obtained based on the determined location of the POI information for each first sub-section in the third division section corresponding to a time point, at which the image information is required, on the UI in real time.

Accordingly, the processor 140 may provide an expert with the image information obtained through the virtual pneumoperitoneum model based on the POI information, which is required in real time during actual surgery, thereby increasing the success rate of surgery through images required in real time.

Alternatively, the processor 140 may display image information obtained from the endoscope inserted into the virtual pneumoperitoneum model based on the determined location of the POI information for each second sub-section, which is a step immediately following the first sub-section, on the UI. That is, the processor 140 may display the image information obtained based on the determined location of the POI information for each second sub-section in the third division section corresponding to a time point, at which the image information is required, on the UI in real time.

Accordingly, the processor 140 may provide the expert with the image information obtained through the virtual pneumoperitoneum model based on the POI information, which is required in the next step of surgery in advance during actual surgery, thereby increasing the success rate of surgery through images required in real time.

The method according to an embodiment of the inventive concept may be implemented by a program (or an application) and may be stored in a medium such that the program is executed in combination with a computer being hardware. Herein, the computer may be the apparatus 10 described above.

The above-described program may include a code encoded by using a computer language such as C, C++, C#, JAVA, a machine language, or the like, which a processor (CPU) of the computer may read through the device interface of the computer, such that the computer reads the program and performs the methods implemented with the program. The code may include a functional code related to a function that defines necessary functions that execute the method, and may include an execution procedure related control code necessary for the processor of the computer to execute the functions in its procedures. Furthermore, the code may further include a memory reference related code on which location (address) of an internal or external memory of the computer should be referenced by the media or additional information necessary for the processor of the computer to execute the functions. Moreover, when the processor of the computer needs to communicate with any other remote computer or any other remote server to perform the functions, the code may further include a communication-related code associated with how to communicate with any other remote computer or server using the communication module of the computer, what information or media should be transmitted or received during communication, or the like.

The steps of a method or algorithm described in connection with the embodiments of the inventive concept may be embodied directly in hardware, in a software module executed by hardware, or in a combination thereof. The software module may reside on a Random Access Memory (RAM), a Read Only Memory (ROM), an Erasable Programmable ROM (EPROM), an Electrically Erasable Programmable ROM (EEPROM), a Flash memory, a hard disk, a removable disk, a CD-ROM, or a computer readable recording medium in any form known in the art to which the inventive concept pertains.

Although embodiments of the inventive concept have been described herein with reference to accompanying drawings, it should be understood by those skilled in the art that the inventive concept may be embodied in other specific forms without departing from the spirit or essential features thereof. Therefore, the above-described embodiments are exemplary in all aspects, and should be construed not to be restrictive.

According to an embodiment of the inventive concept, the inventive concept may recognize a surgery step in a surgical image, may obtain a location of POI information for each surgery step from a 3D-based virtual simulated surgical image, and may provide the location of POI information together with the surgical image. Accordingly, even a specialist who lacks experience in the corresponding surgery may receive an excellent surgical guide in real time, thereby improving a success rate of surgery and significantly reducing the risk of surgery.

Furthermore, the inventive concept may provide an excellent guide to an expert performing surgery by providing a 3D-based virtual surgical simulation environment based on a virtual pneumoperitoneum model for predicting a patient's actual pneumoperitoneum status, and matching a 3D-based virtual surgical simulation environment and an actual surgical image.

The effects of the present inventive concept are not limited to the aforementioned effects, and other effects not mentioned herein will be clearly understood from the following description by those skilled in the art to which the inventive concept pertains.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A method for matching an actual surgical image and a 3D-based virtual surgical simulation environment, which is performed by an apparatus, the method comprising;
    setting point-of-interest (POI) information during surgery at each of surgery steps in a pre-stored surgical image obtained by performing surgery the same as the actual surgical image;
    generating a virtual pneumoperitoneum model of a patient, which is configured to be used for the 3D-based virtual surgical simulation environment, by performing:
        realizing a blood vessel having the same state as the state of the blood vessel in the patient's actual pneumoperitoneum status;
        capturing an Early Arterial Phase (EAP) image and a portal venous phase (PP) image, using the EAP image to divide or restore an artery on a Computed tomography (CT) image, and using the PP image to divide or restore a vein on the CT image;
        additionally dividing or restoring main portions of the artery when the vein is divided or restored, to adjust a location of the artery so as to match major portions of the artery on the vein; and
        matching the vein and the artery depending on a major portion of the artery, wherein the major portion of the artery is POI information, and is a bifurcation of the artery;
    matching the POI information with the virtual pneumoperitoneum model of the patient, wherein the virtual pneumoperitoneum model is displayed on a user interface (UI);
    recognizing a real-time surgery step of the actual surgical image and determining a location of the POI information for the respective recognized surgery step; and
    obtaining and displaying image information, which is captured by moving a location of an endoscope inserted into the virtual pneumoperitoneum model to the same location as the determined location of the POI information, through the UI.

2. The method of claim 1, wherein the setting of the POI information includes:
    dividing the actual surgical image into one or more basic steps based on a surgery object to divide the actual surgical image into the surgery steps;

dividing a surgical operation for a target anatomy or a target object, which corresponds to a surgical purpose of the surgery object, into one or more sub-sections; and dividing one or more unit images included in each of the sub-sections into division sections for each operation by a surgery tool.

3. The method of claim 2, wherein the setting of the POI information includes:

setting the POI information based on the divided sub-sections.

4. The method of claim 3, wherein the determining of the location of the POI information includes:

recognizing a basic step corresponding to the real-time surgery step of the actual surgical image based on a deep learning model;

recognizing a first sub-section corresponding to the real-time surgery step from among a plurality of sub-sections included in the basic step;

determining that one division section corresponding to the real-time surgery step from among a plurality of division sections for the first sub-section corresponds to a time point at which the image information is required;

determining the location of the POI information for the respective first sub-section or the location of the POI information for each second sub-section, which is a step immediately following the first sub-section; and matching information about the determined location of the POI information on the virtual pneumoperitoneum model.

5. The method of claim 4, wherein the obtaining of the image information includes:

moving the location of the endoscope, which is inserted into the virtual pneumoperitoneum model on the UI, based on the determined location of the POI information;

obtaining image information corresponding to a corresponding location from the endoscope; and displaying the obtained image information on the UI at the time point.

6. The method of claim 1, wherein the matching of the POI information includes:

obtaining the virtual pneumoperitoneum model of the patient;

displaying the virtual pneumoperitoneum model on the UI;

inserting the endoscope at a predetermined location of the virtual pneumoperitoneum model; and sequentially matching the POI information with the virtual pneumoperitoneum model in a state where the endoscope is inserted.

7. The method of claim 1, wherein the determining of the location of the POI information includes:

recognizing the real-time surgery step of the actual surgical image based on a deep learning model;

determining the location of the POI information for each recognized surgery step or the location of the POI information for each surgery step immediately following the recognized surgery step; and matching information about the determined location of the POI information on the virtual pneumoperitoneum model.

8. The method of claim 7, wherein the obtaining of the image information includes:

moving the location of the endoscope, which is inserted into the virtual pneumoperitoneum model on the UI, based on the determined location of the POI information;

obtaining image information corresponding to a corresponding location from the endoscope; and displaying the obtained image information on the UI in real time.

9. The method of claim 8, wherein the displaying of the obtained image information on the UI includes:

displaying the image information at a corresponding location of the virtual pneumoperitoneum model; and additionally displaying an indicator indicating a description of the image information.

10. The method of claim 9, wherein the displaying of the obtained image information on the UI includes:

rendering and displaying the image information about portions, which are invisible to naked eyes in the actual surgical image, on the UI in real time.

11. The method of claim 1, wherein the virtual pneumoperitoneum model includes at least one of an actual organ, a blood vessel, a fat, and a muscle in a pneumoperitoneum status of the patient.

12. An apparatus for matching an actual surgical image and a 3D-based virtual surgical simulation environment, the apparatus comprising;

an acquisition unit configured to obtain the actual surgical image and a pre-stored surgical image obtained by performing surgery the same as the actual surgical image;

a display unit configured to display the actual surgical image and a virtual pneumoperitoneum model;

a processor, wherein the processor is configured to:

set point-of-interest (POI) information during surgery at each surgery step in the pre-stored surgical image;

generate a virtual pneumoperitoneum model of a patient, which is configured to be used for the 3D-based virtual surgical simulation environment, by performing:

realizing a blood vessel having the same state as the state of the blood vessel in the patient's actual pneumoperitoneum status;

capturing an Early Arterial Phase (EAP) image and a portal venous phase (PP) image, using the EAP image to divide or restore an artery on a Computed tomography (CT) image, and using the PP image to divide or restore a vein on the CT image;

additionally dividing or restoring main portions of the artery when the vein is divided or restored, to adjust a location of the artery so as to match major portions of the artery on the vein; and matching the vein and the artery depending on a major portion of the artery, wherein the major portion of the artery is POI information, and is a bifurcation of the artery;

sequentially match the POI information with the virtual pneumoperitoneum model of the patient, wherein the virtual pneumoperitoneum model is displayed on a user interface (UI);

recognize a real-time surgery step of the actual surgical image and determine a location of the POI information for the respective recognized surgery step; and obtain and display image information, which is captured by moving a location of an endoscope inserted into the virtual pneumoperitoneum model to the same location as the determined location of the POI information, through the UI.

13. A non-transitory computer-readable recording medium storing a program for matching an actual surgical image and a 3D-based virtual surgical simulation environment, and configured to be coupled to a computer being hardware, the program include instructions to execute the method according to claim 1.

* * * * *